United States Patent
Maschke

(10) Patent No.: US 7,742,826 B2
(45) Date of Patent: Jun. 22, 2010

(54) INTRAVENOUS PACEMAKER ELECTRODE

(75) Inventor: Michael Maschke, Lonnerstadt (DE)

(73) Assignee: Siemens Aktiengesellschaft, Munich (DE)

(*) Notice: Subject to any disclaimer, the term of this patent is extended or adjusted under 35 U.S.C. 154(b) by 1035 days.

(21) Appl. No.: 11/316,065

(22) Filed: Dec. 22, 2005

(65) Prior Publication Data

US 2006/0142830 A1    Jun. 29, 2006

(30) Foreign Application Priority Data

Dec. 23, 2004    (DE)    ........................ 10 2004 062 396

(51) Int. Cl.
*A61N 1/00*    (2006.01)

(52) U.S. Cl. ..................................... 607/122

(58) Field of Classification Search ......... 600/372–375, 600/410; 607/466, 508, 115–156
See application file for complete search history.

(56) References Cited

U.S. PATENT DOCUMENTS

| | | | |
|---|---|---|---|
| 5,030,199 A * | 7/1991 | Barwick et al. | ............... 600/29 |
| 5,904,651 A * | 5/1999 | Swanson et al. | ............ 600/407 |
| 5,968,085 A * | 10/1999 | Morris et al. | ............... 607/116 |
| 6,191,862 B1 | 2/2001 | Swanson et al. | |
| 6,330,467 B1 | 12/2001 | Creighton, IV et al. | |
| 6,445,939 B1 | 9/2002 | Swanson et al. | |
| 6,772,001 B2 * | 8/2004 | Maschke | ..................... 600/423 |
| 2003/0176786 A1 | 9/2003 | Maschke | |
| 2004/0097806 A1 | 5/2004 | Hunter et al. | |
| 2005/0258242 A1 * | 11/2005 | Zarembo | ..................... 235/385 |

FOREIGN PATENT DOCUMENTS

| | | |
|---|---|---|
| DE | 33 00 050 C2 | 7/1984 |
| DE | 102 03 371 A1 | 8/2003 |
| DE | 102 55 957 A1 | 8/2004 |
| EP | 0 882 469 B1 | 12/1998 |

OTHER PUBLICATIONS

L. Binner, V. Hombach, "Technik der Herzschrittmachertherapie", Interventionelle Kardiologie, Angiologie und Kardiovaskularchirurgie, Chapter 9, pp. 165-177, Schattauer Verlag Stuttgart.
G. Sabin, M. Bergbauer, "Herz-Schrittmacher", Aktuelles Wissen Hoechst, Reihe Kardiologie, pp. 56-58.
Biotronik: "Wissenswertes über Herzschrittmacher", http://www.biotronik.com, Siemens AG Medical Solutions, Mar. 7, 2004, pp. 1-6.

* cited by examiner

*Primary Examiner*—George Manuel
*Assistant Examiner*—Shubatra Narayanaswamy

(57) ABSTRACT

An intravenous pacemaker electrode comprises an electrode cable featuring a conductor, a duct and an insulating sleeve as well as an electrode head attached to the distal end of the conductor in order to transmit stimulation pulses, with an OCT catheter being moveable in the duct, and comprising a thread-like guide element as well as an OCT measurement element attached to its distal end.

14 Claims, 3 Drawing Sheets

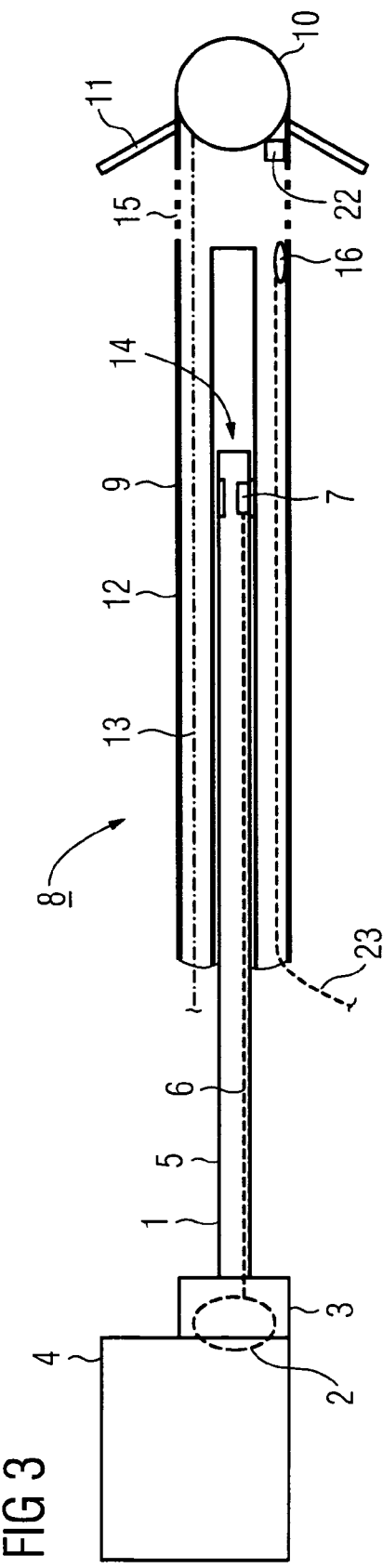
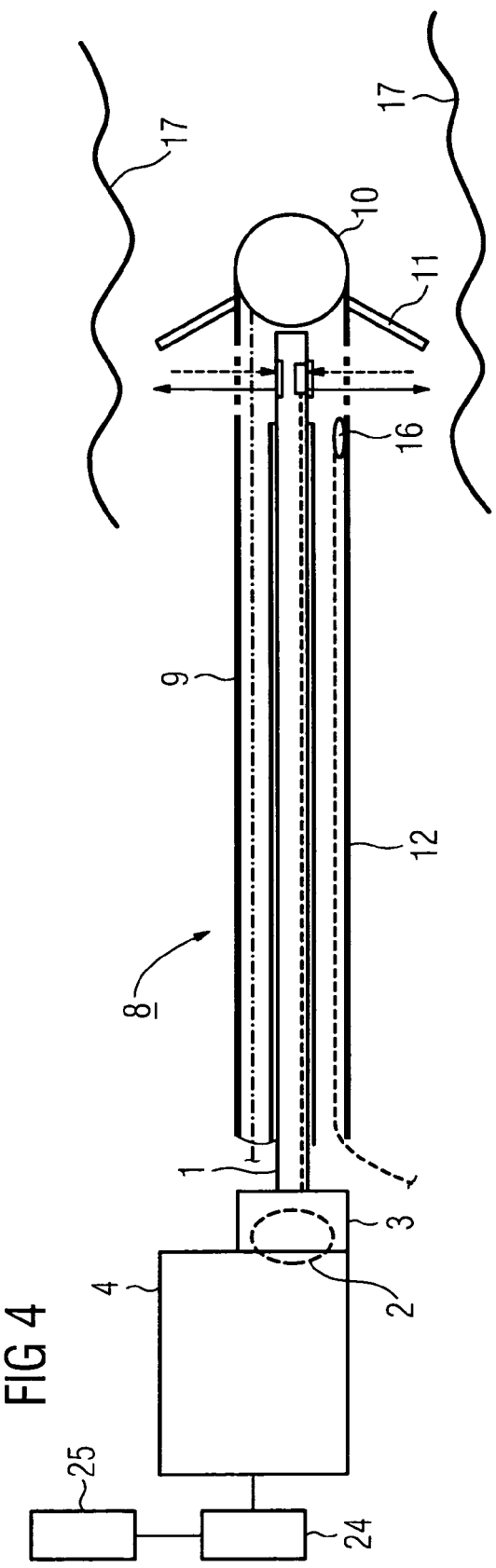

INTRAVENOUS PACEMAKER ELECTRODE

CROSS REFERENCE TO RELATED APPLICATION

This application claims priority of the German application No. 10 2004 062 396.1 DE filed Dec. 23, 2004, which is incorporated by reference herein in its entirety.

FIELD OF THE INVENTION

The invention relates to an intravenous pacemaker electrode with an electrode cable which features a conductor, a channel and an insulation sleeve, with an electrode head for transmission of stimulation pulses being accommodated at the distal end of the conductor.

BACKGROUND OF THE INVENTION

A pacemaker electrode of this type is for example known from DE33 00 050 C2.

Pacemaker electrodes are used to transmit stimulation pulses from a pulse generator to the heart, especially to the atrium and/or to the ventricle. The pacemaker electrodes can be advanced through a vein to the heart with the aid of an introduction instrument, with this process typically being monitored under x-ray illumination. However, especially with the trabecular mesh of the ventricle, this involves very thin soft tissue which can only be seen with difficulty using an x-ray device. In particular it is difficult with known methods to establish whether the electrode tip of the pacemaker electrode is anchored in the desired way on the tissue. This also applies if during the implantation with the aid of a stimulus threshold measuring device the transfer resistance of the pacemaker electrode to the heart muscle is measured.

SUMMARY OF THE INVENTION

The object of the invention is to specify an Intravenous pacemaker electrode which, while being easy to handle, allows an implantation with especially reliable contacting of the myocardium.

In accordance with the invention this object is achieved by an intravenous pacemaker electrode with the features of the claims as well as by a diagnosis and treatment device with the features of the claims.

The inventive intravenous pacemaker electrode features an electrode cable as well as an electrode tip connected to this cable which is provided for transmission of electrical stimulus pulses. A duct as well as a conductor leading to the electrode head run in an electrode cable featuring an insulating sleeve. A catheter which makes possible the emission of visible and/or invisible light can be inserted into the duct of the electrode cable, featuring a thread-like guide element as well as a measurement element for Optical Coherence Tomography (OCT) accommodated at its distal end.

This makes it possible for the pacemaker electrode to simultaneously perform OCT measurements, are known in principle for example from DE 102 55 957 A1 which relates to a medical examination and/or treatment system. In accordance with this known system it is also possible to perform the OCT measurement at the same time as the x-ray investigation.

The guide element of the catheter provided for OCT measurement preferably serves both to advance the OCT measurement element in the electrode cable and also to transmit optical signals. An OCT measurement element is taken to mean a measurement element which is used both for the emission of visible and/or invisible light, especially in the infrared range, and also to accept optical signals. By combining the pacemaker electrode with the OCT measurement element an imaging diagnosis with good resolution in the heart is made possible. This diagnosis is especially advantageous when x-ray illumination is performed simultaneously. The OCT catheter is not permanently connected to the other parts of the pacemaker electrode, but is only introduced into the channel of the electrode cable if required.

Preferably the channel is closed far enough for the OCT catheter not to come into contact with blood or body tissue of the patient. Thus the ultrasound catheter can be used widely, even with different patients. The area of the electrode cable bordering the electrode head is preferably configured such that an OCT measurement is possible to a large extent uninfluenced by the material of the pacemaker electrode. For this purpose an axial space between the distal end of the channel and the electrode tip is advantageous, with the OCT catheter, especially its OCT measurement element being able to be advanced beyond the channel in the direction towards the electrode head. At least one window which is transparent for the light used, especially infrared light, for example a window ring, is arranged in the area of the insulating covering of the electrode cable bordering the electrode head.

According to a preferred development, besides the duct for the OCT catheter, provision is made for a fluid duct suitable for conveying a fluid, especially a rinsing fluid, a fluid transferred with a medicament or a contrast means towards the electrode head, and comprising an outlet opening in front of the electrode head. In contrast, provision can also be made for example to guide the contrast means through the same duct which is also suitable for inserting the OCT catheter. The use of a cooking salt solution for example essentially broadens the diagnostic possibilities of optical coherence tomography. The outlet opening of the fluid duct preferably comprises a sealing device, which prevents body fluids from flowing into the electrode cable, in the manner of a non-return valve.

In addition to the duct for the OCT catheter and if necessary to the fluid duct for the contrast means, the electrode cable comprises an advantageous embodiment of a further guide duct provided for the insertion of a guidewire. The guidewire can also be identical to one of the aforementioned ducts. Independent of the total number of ducts in the electrode cable, provision is made according to a preferred development for an exit opening for the OCT catheter in the region of the electrode head. This allows the OCT measurement element to be moved past the electrode head, provided that the exit opening is located in the electrode head, even out via the electrode head.

Like the outlet opening for the contrast means, the exit opening for the OCT measurement element can also be preferably sealed by means of a valve. Foe example, this valve can be held in a closed state by means of spring force and opened by means of magnetic force. In this case, a magnet, in particular an electromagnet, is preferably arranged in the valve or mechanically coupled thereto.

A particularly reliable sealing of the exit opening for the OCT measurement element can be realized by means of a membrane, which closes the exit opening and is elastic such that the OCT catheter can be moved past the electrode head in the case of an exit opening remaining sealed. In this exemplary embodiment, the exit opening is preferably arranged at the distal end of the electrode head. In this exemplary embodiment, the OCT catheter is preferably rotatably arranged in a protective tube, which—without rotation—can be moved in the electrode cable and therebeyond.

To facilitate the navigation of the pacemaker electrode, the electrode head can be designed such that its movement state can be influenced by means of an external magnetic field. For this purpose, the electrode head preferably contains a magnet, in particular electromagnets, or is mechanically linked to such. An intravascular catheter with an element generating a magnetic field arranged in the catheter sleeve in the area of the catheter tip is known for instance from DE 102 03 371 A1. An electromagnet is preferably used here to generate the magnetic field on the catheter side, which can be powered from outside of the patient and can be varied in terms of field intensity and field direction. A further magnetic system which can be used for medical purposes is known for example from U.S. Pat. No. 6,330,467 B1. This system can also be used with a flexible endoscope or catheter.

In a first embodiment the diagnosis and treatment device according to the invention comprises an intravenous pacemaker electrode as well as an evaluation unit interacting with its OCT measurement element, said evaluation unit being programmed such that influences of the conductor of the electrode cable on the OCT measurement are at least computationally partially eliminated. The intravenous pacemaker electrode thus preferably includes, but not necessarily, the features of the claims.

In a preferred embodiment, the evaluation unit allows the different pacemaker electrodes to be taken into consideration in computations. For this purpose, the evaluation unit is coupled to a data acquisition device which is provided to record data, in particular geometric data of the pacemaker electrode. Different conductor geometries can be practically removed from the images obtained by means of the OCT investigation. In the same way as the geometry of the conductor, other geometrical features of the pacemaker electrode can be taken into account for computations in this way.

Regardless of the features described above or in addition to these features a diagnosis and treatment device, in addition to the intravenous pacemaker electrode, especially with the features of the claims, can include a telemetry module which is arranged in the pacemaker housing to which the electrode cable is connected and features a data connection to the OCT measuring element. The telemetry module allows the OCT measurement data to be read out even after the pacemaker has been implanted. The features of the previously described exemplary embodiments of a diagnosis and treatment device are particularly advantageously combined. In this case the features of the device in accordance with the claims, in other words the computational consideration of the geometry of the pacemaker electrodes, can be reduced within the implanted pacemaker or can be realized in an extracorporeal evaluation unit.

The invention is particularly advantageous in that an imaging diagnosis with good resolution is enabled in the heart by the combination of a pacemaker electrode with an OCT catheter which can be arranged reversibly therein, whereby the risks involved with implantation are considerably reduced by comparison with an implantation exclusively undertaken using x-ray illumination.

BRIEF DESCRIPTION OF THE DRAWINGS

An exemplary embodiment of the invention is described below in further detail with reference to a drawing. The figures show the following outline diagrams:

FIGS. 3 and 4a pacemaker electrode with partially and/or completely inserted OCT catheter, and FIGS. 5 and 6 various embodiments of pacemaker electrodes with an OCT measurement element which can be moved past its electrode head.

DETAILED DESCRIPTION OF THE INVENTION

Figure 1:
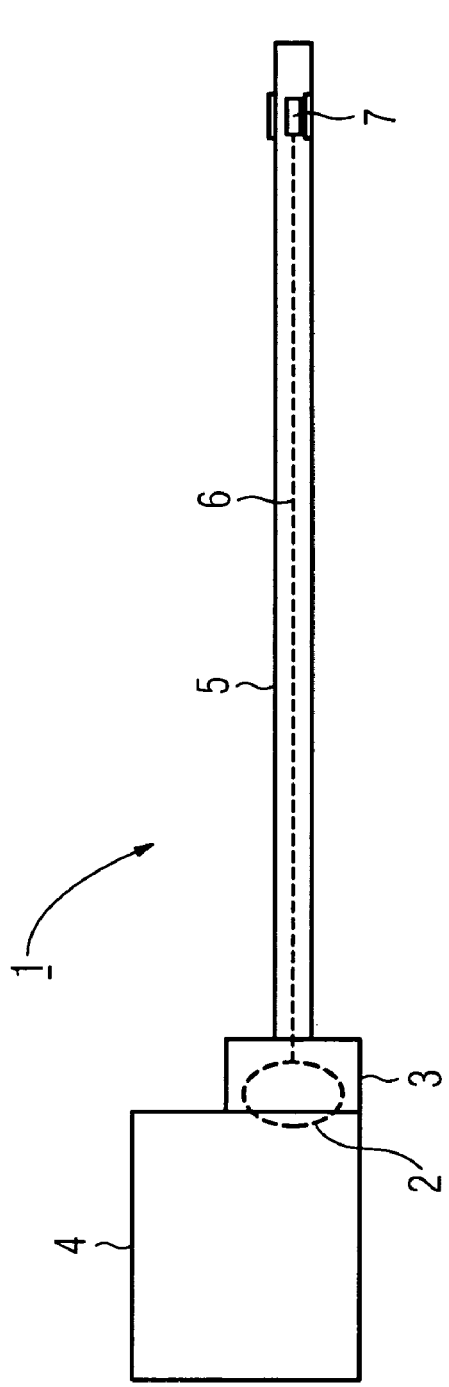
FIG. 1 an OCT catheter for a pacemaker electrode.

Parts which correspond to each other or function identically are provided with the same reference characters in all the figures.

FIG. 1 shows an Optical Coherence Tomography (OCT) catheter 1 for use in an intravenous pacemaker electrode (not shown here in further detail). The term pacemaker electrode is to be understood below in a broader sense and also comprises electrodes for ICDs (implantable cardioverters/defibrillators) for instance.

An optical coherence tomography system (OCT system), which is intended for use in a living body, is known for example from U.S. Pat. No. 6,445,939 B1. In this case a miniaturized optical probe comprises an optical waveguide and a lens which has approximately the same diameter, for example appr. 0.25 mm, as the waveguide.

A further OCT system is known from U.S. Pat. No. 6,191,862 B1. This system operating with rotating optical elements provides option for calibration of the optical measurement as well as synchronization with a motor drive. In this case an optical signal reflected from a cam rotating at a defined speed is compared with a signal output by the sample under examination.

The OCT catheter 1 depicted greatly simplified in FIG. 1 can have any features of the OCT catheters in accordance with the above patents as well as in accordance with DE 102 55 957 A1, including combinations thereof. The OCT catheter 1 can also be used for stimulation electrodes for neurostimulation, which are inserted into the cranium in order to treat a patient with depression or Parkinson's disease for instance.

The OCT catheter 1 according to FIG. 1 is connected to a signal-interface/drive unit 4 for the OCT examination with the aid of a mechanical linking system 3 comprising a rotation coupling 2. The OCT catheter 1 features a sleeve 5 also referred to as a guide element, in which a signal line and drive shaft 6 runs, which is linked to a measurement element suitable for optical coherence tomography 7, abbreviated to OCT measurement element, at the distal end of the OCT catheter. The OCT measurement element 7 can be rotated about its own axis during the examination with the aid of the signal-interface/drive unit 4.

The examination which can be conducted with the aid of the OCT catheter 1 allows a display of tissue structures down to a depth of a few millimeters. In a similar way to ultrasound examination, sectional images are created at right angles to the surface, with this allowing around a hundred times smaller structures to be presented, which includes objects with a size of below 10 μm. The OCT examination stands out by comparison with the ultrasound examination by virtue of its wealth of detail. With the OCT method an interferometric method can be used to filter out those light quantums which were scattered precisely once within the tissue and thereby provide information about the position of the structures there.

Figure 2:
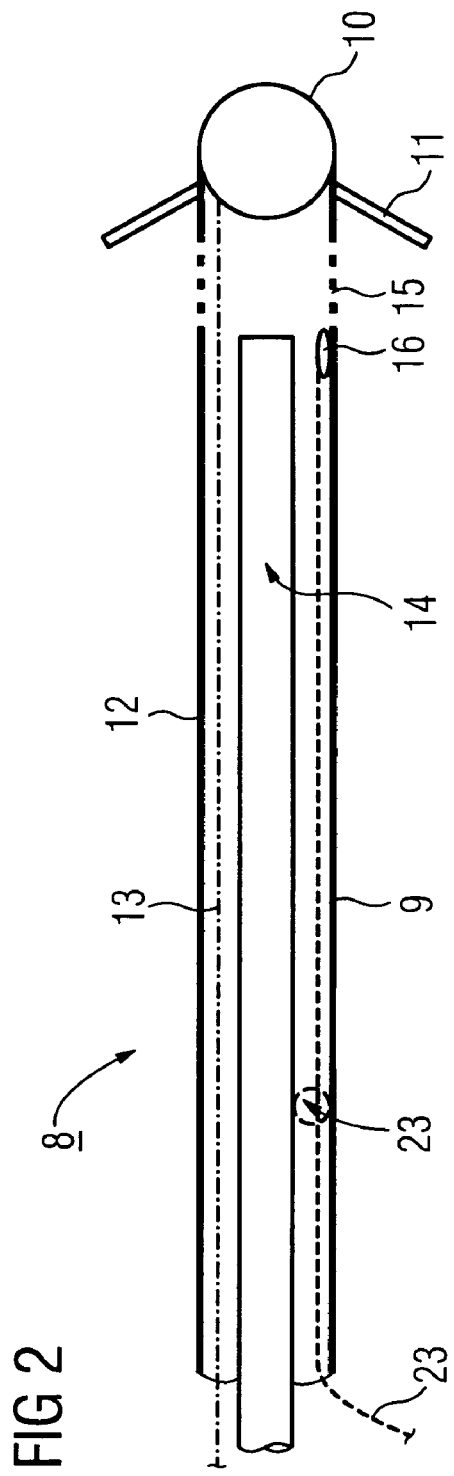
FIG. 2 a pacemaker electrode for use with an OCT catheter according to FIG. 1

FIG. 2 shows an intravenous pacemaker electrode 8 suitable for use with an OCT catheter 1 according to FIG. 1. This is a combination of an electrode cable 9 and an electrode head 10 attached its distal end. The electrode head 10, also known as the electrode tip, serves as a cathode of the pacemaker and is provided for contacting the atrium or the ventricle of the heart. In the embodiment shown, the pacemaker electrode 8 is suitable for instance for a pacemaker which operates with only one electrode as a so-called one-chamber system. Likewise the pacemaker 8 shown can also be used in pacemakers operating with two electrodes, with an electrode being guided to the atrium and to the ventricle in each instance. The pacemaker operating with the pacemaker electrode 8 and not shown in further detail in FIG. 2 can comprise features for instance of an implantable heart support device known from EP 0 882 469 B1, and can also identify and classify the cardial activity in order to transmit stimulation pulses. The pacemaker known from EP 0 882 469 B1 is a device operating using unipolar pacemaker electrodes. In this case, the pacemaker electrode functions as a cathode and the housing of pacemaker as an anode. Likewise the pacemaker electrode 8 displayed section-by-section can also be used as a part of a pacemaker operating with bipolar pacemaker electrodes, with a special anode being arranged in the distal electrode region in this case.

The electrode head 10 comprises a number of fixing aids 11 in the form of fold-out anchor appendages, which engage in the trabecular tissue of the heart chambers in the manner of an anchor and ensure both the mechanical fixing as well as a low-resistance transmission of the stimulation pulses to the myocardium. A possible embodiment of the electrode fixing aids in the form of a wire spring arrangement is known in detail for instance from DE 28 43 096 A1. Notwithstanding the simplified form displayed according to FIG. 2, the fixing aids 11 can also comprises a form known from DE 33 00 050 C2 for instance, which both protects them during the insertion of the electrode through a vein and also prevents body fluid from infiltrating into the electrode. The electrode head 10 including the fixing aids 11 has a surface made of iridium for instance, which exhibits particularly good electrical contacting attributes and thus allows an especially artifact-free perception of signals.

The covering of the electrode cable 9 is formed by an insulating sleeve 12, within which runs a line 13 inter alia connected to the electrode head 10. Furthermore, a duct 14 is located in the electrode cable 9, which is suitable for inserting the OCT catheter 1 (FIG. 1). The distal right-hand end of the duct (in the diagram) is some way away from the electrode head 10, so that the OCT catheter 1 can be moved approximately through the duct 14 towards to the electrode head 10. In this area, the insulating sleeve 12 comprises essentially transparent windows 15 or a window ring for infrared radiation. The line guide of the electrode cable 9 is accordingly adjusted in the region of the window 15 or the window 15. Furthermore, it is possible, as described in greater detail below, to minimize influences of the line guide on the intravascular OCT measurement in a control or software-specific manner.

The pacemaker electrode 8 is also suitable for illuminating a fluid, for example a cooking salt solution as a rinsing fluid and for this purpose features an outlet opening 16 in the insulating sleeve 12 near to the electrode head 10, next to the windows 15. The fluid flowing through the electrode cable 9 to the outlet opening 16 which can also contain a contrast means and/or medicament, is indicated by the dashed line. The outlet opening 16 is designed as a miniaturized non-return valve, thereby intentionally allowing the fluid to flow out directly from the pacemaker electrode 8 into the heart chamber, but nevertheless preventing the blood from infiltrating into the lumen of the electrode cable 9. Thus the OCT catheter 1 does not come into contact with the body fluid of the patient in cases in which during the OCT examination a fluid used for diagnostic and/or therapeutic is supplied and can thus be readily widely used. The non-return valve 16 is preferably manufactured using nanotechnology methods, in other words in particular with methods used in the field of semiconductor technology, including etching technology and lithography. The same applies to other miniaturized parts of the intravenous pacemaker electrode 8.

The lumen, through which a given fluid is directed to the exit opening 16, can be identical to the duct 14 for the OCT catheter 1 or to another hollow space, or, as in the exemplary embodiment according to FIG. 2, can be designed as a special fluid duct 23. The same applies to the potential combination of the duct 14 with a duct for a guidewire of the pacemaker electrode 8. In each case, contrast means can be fed through the duct 14 in order to improve the x-ray and/or OCT display. Sealing plugs are provided at the end of the pacemaker electrode 8 which is not shown, to which the actual pacemaker is to be connected. The pacemaker electrode 8 preferably comprises a separate duct 14 which is solely provided for inserting the OCT catheter 1 and is preferably located in the middle of the electrode cable 9, as shown in FIG. 2. The centrical arrangement of the duct 14 is particularly advantageous in that the OCT measurement element 7 is thus centered in the electrode cable 9. Silicon or polyurethane can be used as the wall material of the duct 14 for instance, as well as for other insulating parts of the electrode cable 9.

FIGS. 3 and 4 show the introduction of the OCT catheter 1 into the electrode cable 9 of the pacemaker electrode 8. Tissue walls 17 are also indicated in FIG. 4 which are to be examined by optical coherence tomography (OCT). The OCT measurement element 7 which is arranged at the distal end of the OCT catheter 1 transmits and receives OCT signals, with transmitted signals being indicated in FIG. 4 by continuous arrows and reflected signals by dashed arrows. The OCT measurement element 7 is supported so that it can rotate in the sleeve 5 also referred to as a guide element. Unlike the depiction in the diagram, when the electrode cable 9 is advanced, the fixing aids 11 are folded towards the electrode head 10. It is particularly advantageous that in order to rotate the OCT measurement element 7 about the longitudinal axis of the electrode cable 9, this does not need to be completely rotated, in other words a rotation of the OCT measurement element within the sleeve 5 also referred to as a guide element is sufficient.

Unlike the depiction shown in FIGS. 3 and 4, the OCT catheter can also be combined with a special catheter for diagnostic or treatment purposes. This is just as advantageous during use as part of the pacemaker electrode 8, such that the OCT catheter 1 does not come into contact with patients' tissue or body fluid. As shown symbolically in FIG. 3, the electrode head 10 has a magnet 22, preferably an electromagnet which can be controlled by means of the electrode cable 9, which allows the pacemaker electrode 8 to be magnetically navigated in the body of the patient in conjunction with an external magnetic field.

As can be seen from FIG. 4, the infrared light of the measurement element 7 radiates through in an area adjacent to the electrode head 10 in which the conductor 13 also runs. An influencing of the recorded OCT data by the electrode cable 9 is thus not be entirely avoided. This influencing can however be minimized on automatic evaluation of the OCT signals, especially by software measures. In particular the geometry of the electrode cable 9 can be taken into account in the computations, with different possible embodiments of pacemaker electrodes 8 able to be included specifically in the evaluation. For this purpose an evaluation unit 24 with a data link to the measuring element 7 provided for evaluation of the OCT signals is connected to a data acquisition device 25, for example in the form of a scanner. The geometric data and other relevant data of the potentially used pacemaker electrode 8 is stored in a database, and can be assigned to a barcode which is applied to the packaging of the pacemaker electrode 8 and is read with the aid of the data acquisition device. The evaluation unit uses this data to generate from the signals obtained by means of the OCT measurement element 7 at least essentially artifact-free images, especially those eliminating influences of the conductor 13.

Figure 5:
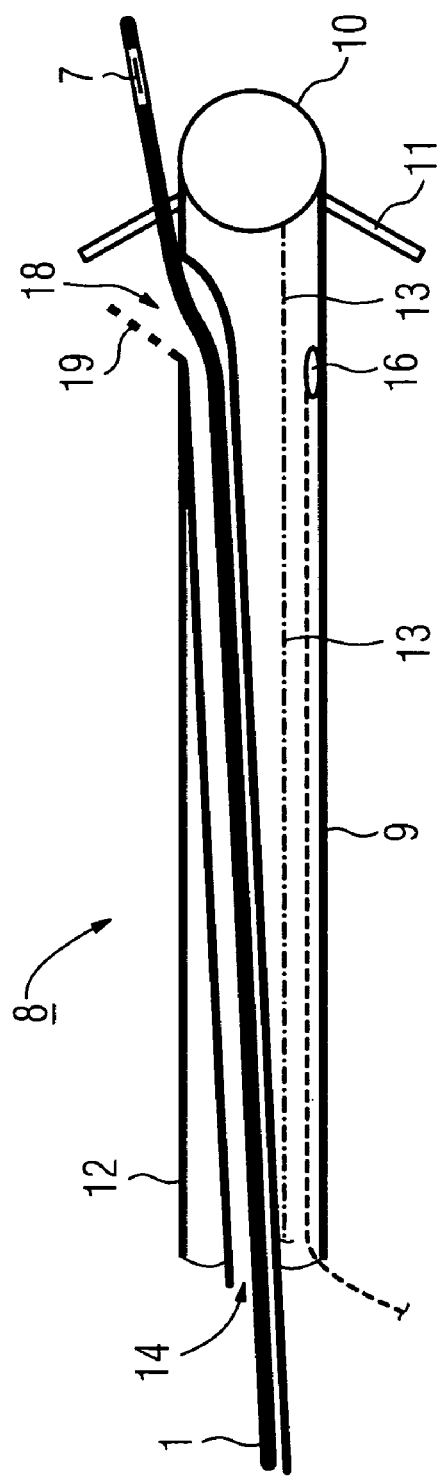
Figure 6:
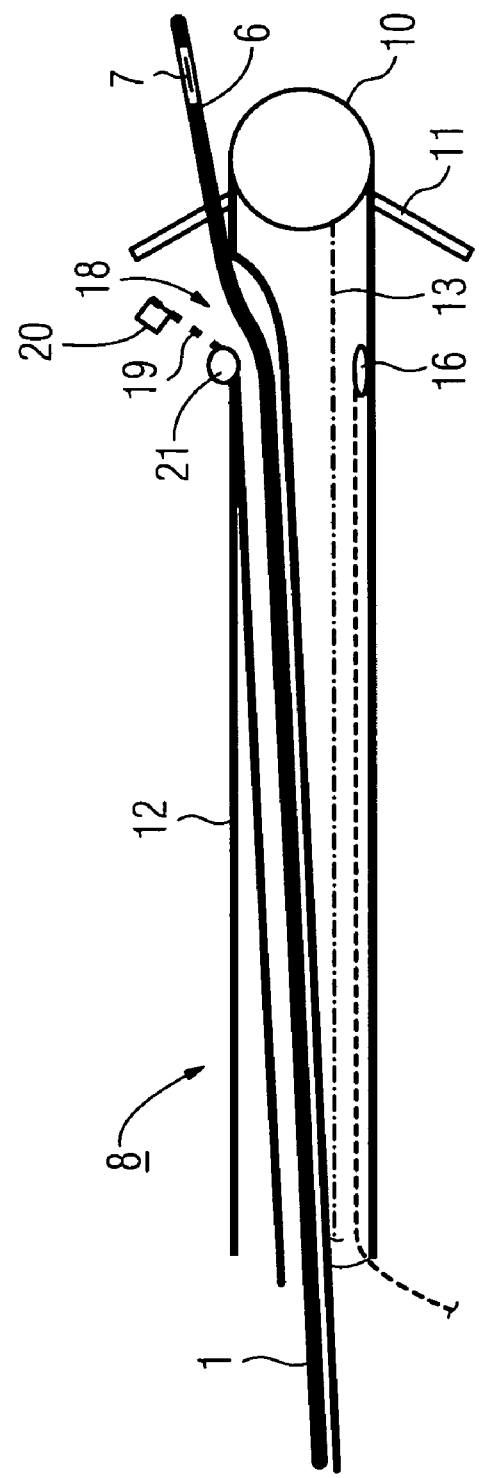

FIGS. 5 and 6 show developments of the pacemaker electrode 8, which allows wider use of the OCT catheter 1. In this case the insulating sleeve 12 features a valve 19 near to the electrode head 10, approximately at the height of the outlet opening 16, said valve sealing an exit opening 18 of the duct 14 in a closed state. The OCT measurement element 7 can be moved out of the electrode cable 9 and moved past the electrode head 10 by means of this valve 19, which is designed approximately according to the principle of a heart beat or in the manner of a drainage hole of a sailing boat. The valve 19 is opened for instance by force effect of the OCT measurement element 7 when the OCT catheter 1 is advanced (FIG. 5). In the embodiment according to FIG. 6, the valve 19 comprises a magnet 20 and a support with a spring element 21, which retains the valve 19 in a closed state without further force effect. The magnet 20, preferably a permanent magnet, serves to open the valve 19 with the aid of an strong external magnetic field if necessary. Independent of the detailed mode of operation of the valve 19, this is preferably designed as a non-return valve, so that no blood can infiltrate into the duct 14 of the electrode cable 9.

The invention claimed is:

1. The intravenous pacemaker electrode, comprising:
   an electrode cable, comprising:
      a conductor,
      a channel,
      an insulating sleeve,
   a pacemaker electrode head attached to a distal end of the electrode cable configured to transmit a plurality of stimulation pulses to a heart of a patient;
   an OCT catheter that moves in a duct and has a thread-like guide element; and
   an OCT measurement element attached to a distal end of the OCT measurement element for optical coherence tomography, wherein a distal end of the duct is axially distanced from the electrode head such that the OCT catheter can be moved beyond the duct towards the electrode head via an exit opening.

2. The pacemaker electrode in accordance with claim 1, including a window of the insulating sleeve is transparent for light of the measurement element and arranged between a distal end of the duct and the electrode head.

3. The pacemaker electrode in accordance with claim 1, including a fluid duct comprising an outlet opening in front of the electrode head and suitable for transferring a liquid with a medicament or a contrast towards the electrode head.

4. The pacemaker electrode in accordance with claim 3, wherein the outlet opening comprises a sealing device.

5. The pacemaker electrode in accordance with claim 4, wherein the sealing device of the outlet opening is configured as a non-return valve.

6. The pacemaker electrode in accordance with claim 1, including a duct for a catheter which is separated from a guide duct and provided for the insertion of a guidewire.

7. The pacemaker electrode in accordance with claim 1, wherein an exit opening for the OCT catheter is arranged in the region of the electrode head.

8. The pacemaker electrode in accordance with claim 7, wherein the exit opening is closed by a valve.

9. The pacemaker electrode in accordance with claim 8, wherein the valve is magnetically activated.

10. The pacemaker electrode in accordance with claim 1, including a magnet is mechanically connected to the electrode head for influencing the movement by an external magnetic field.

11. The pacemaker electrode in accordance with claim 10, wherein an electromagnet is provided as the magnet.

12. A diagnosis and treatment device, comprising:
    an intravenous pacemaker electrode, comprising:
       an electrode cable, comprising,
          a conductor,
          a channel,
          an insulating sleeve,
       an electrode head attached to a distal end of the electrode cable configured to transmit a plurality of stimulation pulses to a heart of a patient;
    an OCT catheter that moves in a duct and has a thread-like guide element;
    an OCT measurement element attached to the distal end for optical coherence tomography; and
    an evaluation unit that interacts with the OCT measurement element of the pacemaker electrode and is programmed such that an influence of the pacemaker electrode is at least partially eliminated by the programming.

13. The device in accordance with claim 12, including a data acquisition device coupled to the evaluation unit is provided to record geometric data of the pacemaker electrode.

14. The device in accordance with claim 13, including a scanner for reading a barcode or an RFID chip on a packaging of the pacemaker electrode is provided as a data acquisition device.

* * * * *